United States Patent [19]

Uschold

[11] 4,385,187
[45] May 24, 1983

[54] PERFLUOROKETOVINYL ETHERS AND COPOLYMERS THEREFROM

[75] Inventor: Ronald E. Uschold, West Chester, Pa.

[73] Assignee: E. I. Du Pont de Nemours and Company, Wilmington, Del.

[21] Appl. No.: 279,024

[22] Filed: Jun. 30, 1981

[51] Int. Cl.³ .................... C07C 45/41; C07C 49/227
[52] U.S. Cl. .................... 568/398; 568/415; 521/38
[58] Field of Search ............... 568/415, 414, 398, 397

[56] References Cited

U.S. PATENT DOCUMENTS

| | | | |
|---|---|---|---|
| 3,114,778 | 12/1963 | Fritz et al. | 260/614 |
| 3,250,808 | 5/1966 | Moore et al. | 260/535 |
| 3,326,984 | 6/1967 | Anderson et al. | 260/614 |
| 3,513,203 | 5/1970 | Sianesi et al. | 568/397 |
| 3,798,273 | 3/1974 | Cargill | 568/398 |
| 3,847,978 | 11/1974 | Sianesi et al. | 260/535 H |
| 4,126,588 | 11/1978 | Ukihashi et al. | 521/31 |
| 4,131,740 | 12/1978 | England | 560/180 |
| 4,138,373 | 2/1979 | Ukihashi et al. | 521/38 |
| 4,138,426 | 2/1979 | England | 260/465.6 |
| 4,151,200 | 4/1979 | Yamabe et al. | 260/544 F |
| 4,153,804 | 5/1979 | Yamabe et al. | 560/183 |
| 4,267,364 | 5/1981 | Grot et al. | 560/183 |
| 4,304,927 | 12/1981 | Krespan | 568/397 |

FOREIGN PATENT DOCUMENTS

| | | |
|---|---|---|
| 5015410 | 7/1978 | Japan . |
| 54-109918 | 8/1979 | Japan . |

OTHER PUBLICATIONS

R. E. Banks, "Fluorocarbons and Their Derivatives," Elsevier (1970), p. 22.
Hudlicky, "Chemistry of Organic Fluorine Compounds," MacMillan (1962), p. 271.
Krespan et al., Fluroine Chem. Revs. 1 (1), 145 (1967), p. 152.
Simmons et al., JACS 82, 2288 (1960).
Sullivan, *J. Org. Chem.* 34 (6), 1841 (1969).

*Primary Examiner*—James H. Reamer

[57] ABSTRACT

Perfluoroketovinyl ether of the formula (as in claim 1) wherein n is an integer 1 to 4, copolymers of such ether and a fluorinated monomer, such as tetrafluoroethylene; ion-exchange resins of such copolymers; and ion-exchange membranes of such resins.

5 Claims, No Drawings

PERFLUOROKETOVINYL ETHERS AND COPOLYMERS THEREFROM

DESCRIPTION

TECHNICAL FIELD

This invention relates to perfluoroketovinyl ethers and to perfluorinated copolymers prepared from such ethers.

BACKGROUND

U.S. Pat. No. 4,138,426 discloses perfluorovinyl ether carboxylates of the formula

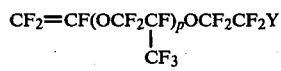

wherein Y is $-CO_2R$, $-CO_2H$, $-CO_2M$ or $-CN$, R is $C_1$ to $_6$ alkyl, M is alkali metal, ammonium or quaternary ammonium and p is an integer 1 to 5.

Japanese Publication J5 No. 5015-410 discloses the thermal decomposition, at 230°–400° C., of metal salts of the formula

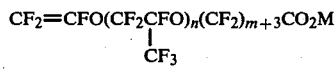

wherein M is alkali metal, n is 0 or an integer 1 to 3, m is 0 or an integer 1 to 4 and $n+m \neq 0$. The products are divinyl ethers of the formula

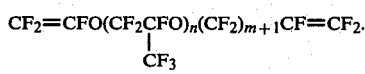

R. E. Banks, "Fluorocarbons and Their Derivatives", Elsevier (1970), page 22, discloses the solventless pyrolysis of perfluorovinyl carboxylic acid salts to perfluorodiolefins at 100°–450° C. and 0.01 mm Hg (1.3 Pa), for example, $CF_2=CFCF_2CF_2CO_2Na$ to $CF_2=CFCF=CF_2$, $CO_2$ and NaF.

It is known that in the pyrolysis of acyl fluorides

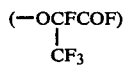

or the corresponding carboxylic acid salts

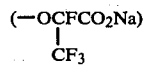

to vinyl ethers ($-OCF=CF_2$), $CO_2$ and NaF, use of solvents such as tetraglyme is optional but may facilitate pyrolysis at lower temperatures. U.S. Pat. No. 3,114,778 discloses the pyrolysis of perfluorodicarboxylic acid salts to divinyl ethers, for example,

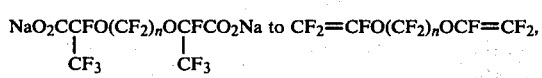

$CO_2$ and NaF, without solvent, at 170°–250° C. or, using solvent, at temperatures as low as 100° C. U.S. Pat. No. 3,326,984 discloses the pyrolysis of an unsymmetrical perfluorodicarboxylic acid salt of the formula

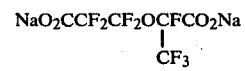

to the divinyl ether $CF_2=CFOCF=CF_2$, without solvent, at 200°–300° C., or in an inert polar solvent such as tetraglyme, at 100°–200° C. In neither patent are different products or different product distributions, in the presence or absence of solvent, disclosed.

Hudlicky, "Chemistry of Organic Fluorine Compounds", MacMillan (1962), page 271, discloses the pyrolysis of salts of perfluoromonocarboxylic acids, both in the presence and absence of ethylene glycol as the solvent. For example, potassium perfluoropentanoate yields $CF_3CF=CF-CF_2$ and $CF_3CF_2CF=CF_2$ at 165°–200° C., but yields $CF_3CF_2CF_2CF_2H$ at 170°–190° C. in the presence of ethylene glycol.

U.S. Pat. No. 3,847,978 discloses perfluoroketoacyl fluorides of the formula

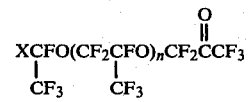

wherein n is 1 to 50 and X is COF or $CO_2H$. No ketovinyl ethers are disclosed.

DISCLOSURE OF INVENTION

For further conprehension of the invention, and of the objects and advantages thereof, reference may be made to the following description and to the appended claims in which the various novel features of the invention are more particularly set forth.

This invention resides in the perfluoroketovinyl ether of the formula

(1)

wherein n is an integer of 1 to 4, and in copolymers of the ether 1 and a fluorinated vinyl monomer such as tetrafluoroethylene, chlorotrifluoroethylene, trifluoroethylene, perfluoroalkylvinyl ether wherein the perfluoroalkyl group contains 1 to 4 carbon atoms, vinylidene fluoride, or combinations of these vinyl monomers. The invention also resides in molded objects of such copolymers, for example, ion-exchange membranes. The invention further resides in a process for preparing the ether 1 from the known perfluorovinyl ether carboxylic acid salt of the formula

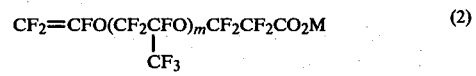
(2)

wherein m is an integer 2 to 5 and M is an alkali or alkaline earth metal.

The ketovinyl ether 1 is prepared by heating the salt of formula 2 in an aprotic ether solvent, such as a glyme (i.e., mono-, di-, tri- or tetraethyleneglycol dimethyl ether), preferably tetraglyme, at a temperature of 130° to 300° C., preferably 170° to 230° C. Preferably, the solvent should be higher boiling than the reaction products. It is essential to the preparation of the ketovinyl ether 1 that the carboxylic acid salt 2 be pyrolyzed in an appropriate solvent. If salt 2 is pyrolyzed in the absence of solvent, the ketovinyl ether is formed in very minor amounts, if at all.

It is important that the solvent and the salt 2 be moisture-free. The presence of water or other substances which can yield a proton during pyrolysis lowers the yield of the desired ether 1 by producing the hydrogen-capped by-product of the formula

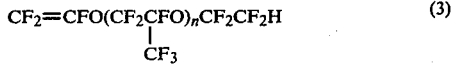

(3)

wherein n is an integer 1 to 4. The formation of this by-product is demonstrated in Examples 1 and 4 and in Experiment 1.

Various methods of drying the salt 2 can be used, including evaporation of water, azotropic distillation of water with toluene and neutralization in methanol solution followed by evaporation of methanol. In all these cases final drying in a vacuum oven is required to ensure complete removal of water or methanol. Neutralization in methanol is preferred because less foam is generated in the drying process, and the lower boiling point and lower heat of vaporization of methanol relative to water increases the drying rate. Solvents for the pyrolysis are dried by standard methods for drying organic liquids; distillation from sodium hydride is convenient.

Preferred salts are formula 2 wherein M is Na. Other alkali metal or alkaline earth metal salts can be employed, but they are generally more difficult to dry adequately. Example 4 illustrates the use of a calcium salt. An oven temperature of 140° C. was required to dry the calcium salt, in contrast to 100° C. typically used to dry the sodium and lithium salts. Even at this high temperature in Example 4, the calcium salt still contained about 0.5 mole of water per mole of salt. This undoubtedly contributed to the comparatively low yield of the desired ketovinyl ether 1 and the larger amount of hydrogen-capped by-product. The lithium salt (Example 5) is also more difficult to dry than the sodium salt and is more hygroscopic. Sodium salts are preferred over potassium and other alkali metal salts, also, for economic reasons.

As already shown in formula 2 for the perfluorovinyl ether carboxylic acid salt, m is at least 2. As shown in Experiment 1, a pyrolysis of a salt of the formula wherein m is 1 yields as the principal product an acyl fluoride. Pyrolysis of a salt of the formula wherein m is 0 yields a divinyl ether, as disclosed in the art.

Pressure is not a critical variable for the pyrolysis of the salt 2. A pressure above or below atmospheric pressure can be employed. Atmospheric or subatmospheric pressure is preferred, however, because of the comparative ease of recovering the distillable reaction products.

Use of a catalyst in the pyrolysis of the salt 2 is neither required nor desirable.

The perfluoroketovinyl ether 1 can be copolymerized with a fluorinated vinyl monomer such as tetrafluoroethylene, chlorotrifluoroethylene, trifluoroethylene, perfluoroalkylvinyl ether wherein the perfluoroalkyl group contains 1 to 4 carbon atoms, vinylidene fluoride, or combinations of these vinyl monomers. Well-known, free radical-initiated addition copolymerization methods can be employed.

Copolymers prepared from the ketovinyl ether of formula 1 and a vinyl monomer contain repeat units of the formula

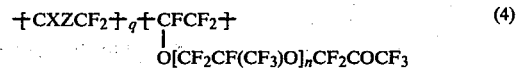

(4)

wherein X is F or H; Z is F, H, Cl or OR wherein R is perfluoroalkyl of 1 to 4 carbon atoms; n is an integer 1 to 4; and q is about 3 to about 200, preferably about 6 to about 50. The copolymers are moldable, as demonstrated by the preparation of films therefrom by hot-pressing. The copolymers can be hydrolyzed by treatment with either dilute (for example, 10 weight %) aqueous mineral acid or aqueous alkali. The ion-exchange properties of the copolymer can be demonstrated by hydrolyzing the copolymer in 10% aqueous sulfuric acid to convert the carbonyl group to a gem diol, then immersing the washed, acid-hydrolyzed copolymer in 10% aqueous sodium chloride solution containing an excess of sodium hydroxide, and backtitrating the residual alkali.

The copolymers having repeat units of formula 4, or their hydrolysates, can be converted to carboxyl-functional copolymers by treatment with strong alkali (haloform reaction). The resultant copolymers have repeat units of formula 4 except that the chain end group is $CO_2M$ instead of $COCF_3$, M being an appropriate cation, and they are useful as ion-exchange resins and as ion-exchange membranes in chloroalkali electrolysis cells. A membrane of the copolymer having repeat units of formula 4 can be used in such a cell because the copolymer is rapidly hydrolyzed, then subsequently converted to the carboxylate —$CO_2M$) form in situ in the strongly alkaline medium of the cell. Both hydrolysate and carboxylate forms have ion-exchange properties as indicated above. Preferably, the membranes are hydrolyzed prior to cell use.

The copolymers are dyeable with dyes containing an NH or OH moiety and they are crosslinkable with compounds containing a plurality of NH and/or OH moieties by virtue of known chemistry of the perfluoroketo group. The hydrolyzed copolymers are similarly dyeable, and they can be crosslinked by reaction with isocyanates.

In the following examples which illustrate the invention, parts and percentages are by weight unless otherwise indicated.

EXAMPLE 1

This example describes the preparation of a perfluoroketovinyl ether of formula 1 from the sodium salt of formula 2.

100 Grams (0.170 mole) of methyl perfluoro-5,8-dimethyl-4,7,10-trioxa-11-dodecenoate was placed in a flask with 100 ml of water. 6.9 Grams (0.173 mole) of sodium hydroxide was dissolved in a small amount of water and added dropwise, with stirring, to the flask. The reaction mixture became a slurry. When addition of the sodium hydroxide was completed, the water was evaporated on a steam bath under a stream of nitrogen. The sodium salt obtained was then dried in a vacuum oven at 120° C.

The salt (50 g) thus obtained was added to a dry 250 ml flask containing a magnetic stirring bar and a side arm with a thermometer. The flask was flushed with nitrogen and connected to a distillation head; 100 ml of tetraglyme was added to the flask. The contents of the flask were heated strongly. By the time the temperature of the reaction mixture reached 160° C., the salt had dissolved and gas evolution was noted. Heating was continued and the temperature rose to 200° C. Gas evolution increased with the temperature and product began to distill. Heating was continued until distillation stopped. A total of 22 g of a product mixture was collected. Analysis of the product by gas chromatography showed the presence of two components accounting for 65% and 35% of the mixture, respectively. The components of the mixture were separated by fractional distillation and were identified by their fluorine nuclear magnetic resonance spectra and by their infrared spectra. The major product was perfluoro-5-methyl-8-oxo-3,6-dioxa-1-nonene and the minor product was 11H-perfluoro-5,8-dimethyl-3,6,9-trioxa-1-undecene.

EXAMPLE 2

This example describes the preparation of a perfluoroketovinyl ether of formula 1 from the sodium salt of formula 2.

52 Grams (0.0885 mole) of the starting ester used in Example 1 was placed in a flask with 50 ml of methanol containing 3.54 g (0.0885 mole) of sodium hydroxide. The mixture was warmed with stirring until the pH was 6-7 as indicated by test paper. Most of the methanol was removed in a rotary evaporator to yield a viscous oil. The remaining methanol was removed on a steam bath under a stream of nitrogen. The white solid sodium salt which was obtained, after drying in a vacuum oven at 100° C., weighed 47.2 g. It was placed in a flask along with 100 ml of tetraglyme and heated to 200°-210° C. The product perfluoro-5-methyl-8-oxo-3,6-dioxa-1-nonene was distilled from the reaction mixture as it formed; yield, 13.8 g.

EXAMPLE 3

This example describes the preparation of a perfluoroketovinyl ether of formula 1 from the sodium salt of formula 2.

Sodium perfluoro-5,8,11,14-tetramethyl-4,7,10,13,16-pentaoxa-17-octadeceneoate was prepared by adding 12.5 g of the corresponding methyl ester and 10 ml of water containing 0.55 g of sodium hydroxide to a flask containing 50 ml of water. The contents of the flask was warmed gently and stirred until a viscous solution was formed of neutral pH. The water was evaporated and the salt remaining was dried at 110° C. in a vacuum oven.

The dry salt was pyrolyzed at 200°-210° C. in 50 ml of tetraglyme distilled from sodium hydride. When the pyrolysis was completed, the pressure in the apparatus was gradually lowered by means of a vacuum pump to 155 mm of Hg (20.6 kPa). Product distilled at 145°-155° C. was collected; 5.2 g. Gas chromatographic analysis showed it to be a mixture, with the major product accounting for 70% of the mixture. The major product which was isolated by fractional distillation and identified from its infrared and fluorine nuclear magnetic resonance spectra was perfluoro-5,8,11-trimethyl-14-oxo-3,6,9,12-tetraoxa-1-pentadecene.

EXAMPLE 4

This example describes the preparation of a perfluoroketovinyl ether of formula 1 from the calcium salt of formula 2.

200 Grams (0.340 mole) of the starting ester used in Example 1 was mixed with 15 g (0.375 mole) of sodium hydroxide dissolved in 500 ml water. The mixture was stirred until it was neutral; then, 38 ml of concentrated hydrochloric acid was added. The reaction mixture separated into two layers. The bottom layer was removed and the top layer was extracted with three 200 ml portions of diethyl ether. The ether extracts were combined with the bottom layer from above and dried over magnesium sulfate. The ether was evaporated to yield 179.7 g of perfluoro-5,8-dimethyl-4,7,10-trioxa-11-dodecenoic acid.

50 Grams (0.0871 mole) of the acid and 3.2 g (0.0432 mole) of calcium hydroxide were shaken with 300 ml of water until a gelatinous precipitate formed. The precipitate was isolated and taken up in methanol to yield a turbid solution which was filtered to yield a clear solution of neutral pH. The methanol was evaporated to yield the white solid calcium salt which was dried at 110° C. in a vacuum oven for 24 h to constant weight. Additional water was driven off by drying another 23 h at 140° C. A portion (33 g) of the calcium salt was pyrolyzed in tetraglyme freshly distilled from sodium hydride. Analysis of the product which was collected by distillation, 8.8 g, showed that 19% of it was perfluoro-5-methyl-8-oxo-3,6-dioxa-1-nonene and 38% was 11H-perfluoro-5,8-dimethyl-3,6,9-trioxa-1-undecene.

EXAMPLE 5

This example describes the preparation of a perfluoroketovinyl ether of formula 1 from the lithium salt of formula 2.

1.3 Grams (0.043 mole) of lithium oxide was dissolved in 300 ml of water. 50 Grams (0.087 mole) of perfluoro-5,8-dimethyl-4,7,10-trioxa-11-dodecenoic acid prepared as in Example 4 was dissolved in 150 ml of methanol and mixed with the lithium oxide solution. The pH of the mixture was neutral. The solvents were evaporated and the salt was dried 6 days in a vacuum oven at 110° C. At 110° C. the dry salt is a plastic mass which hardens to a hygroscopic glass at room temperature. 25.9 Grams of the lithium salt was placed in a flask and pyrolyzed in tetraglyme as described in Example 1. Product distilled to yield 9.0 g of material which was analyzed and shown to contain 76% of the ketovinyl ether perfluoro-5-methyl-8-oxo-3,6-dioxa-1-nonene.

EXAMPLE 6

This example describes the preparation of a copolymer of tetrafluoroethylene and the perfluoroketovinyl ether of formula 1. It also demonstrates the utility of the copolymers of the invention as ion-exchange resins.

A 500 ml pyrex pressure bottle containing 10.0 g of perfluoro-5-methyl-8-oxo-3,6-dioxa-1-nonene, 11 ml of $CFCl_2CF_2Cl$ and 50 mg of perfluoropropionyl peroxide was placed on a Parr pressure reaction apparatus. The apparatus was pressured to 60 psig (414 kPa) with tetrafluoroethylene and a constant pressure of 60 psig (414 kPa) was maintained by means of a regulator. The polymerization was allowed to proceed for 3 h. The apparatus was vented and 1.84 g of polymer was isolated by evaporating solvent and unused monomers. A sample of the polymer was hot pressed into a film. An infrared spectrum of the film showed a carbonyl band at 1810 cm$^{-1}$, characteristic of the keto group. A sample of the film was heated in 10% sulfuric acid on a steam bath for 2 h and then washed neutral. The sample was soaked in 10% aqueous sodium chloride containing 1.011 meq of sodium hydroxide. Titration of excess sodium hydroxide with standard acid showed the equivalent weight of the polymer to be 1401. Thus, q in the aforesaid formula 4 is approximately 9.9.

EXAMPLE 7

This example describes the preparation of a copolymer of tetrafluoroethylene and the perfluoroketovinyl ether of formula 1.

A 75 cc pressure bomb was charged with a weighed amount of perfluoro-5-methyl-8-oxo-3,6-dioxa-1-nonene and 10 ml of $CFCl_2CF_2Cl$ containing perfluoropropionyl peroxide. The bomb was closed and cooled in dry ice/acetone. The bomb was then evacuated and repressurized with nitrogen. This nitrogen flush procedure was repeated three times and then 10.0 g of tetrafluoroethylene was charged to the bomb. The bomb was placed on a shaker and warmed to 60° C. for 3 h. After cooling to room temperature the bomb was vented and opened. The polymer, swollen with solvent, was removed and dried. Equivalent weights were determined as described in Example 6. Experimental data are presented below for two runs.

| Run | Perfluoro-propionyl peroxide (mg) | perfluoro-5-methyl-8-oxo-3,6-dioxa-1-nonene (g) | Pressure (psig) | Pressure (kPa) |
|---|---|---|---|---|
| A | 5 | 10.0 | 125–105 | 862–724 |
| B | 26 | 40.0 | 178–110 | 1228–758 |

| Run | Reaction Time (h) | Copolymer (g) | Equivalent Weight | q |
|---|---|---|---|---|
| A | 3 | 1.7 | >12,000 | >115 |
| B | 1 | 11.9 | 1,915 | 15 |

EXPERIMENT 1

This experiment shows the different result that is obtained when the starting salt contains only one hexafluoropropylene oxide unit, that is, when m in formula 2 is one (outside the invention).

67 Grams of sodium perfluoro-5-methyl-4,7-dioxa-8-nonenoate was placed in a flask and 100 ml of tetraglyme was vacuum distilled from sodium hydride into the flask. The flask was connected in sequence to a distillation head and a trap cooled by dry ice/acetone. The mixture was heated as described in Example 1. The first evolution of gas was noted at 149° C., with vigorous evolution occurring at 175° C. Product distilled from the reaction mixture. A total of 21.2 g was collected in the receiver of the distillation head. This product was shown to be perfluoro-5-methyl-4,7-dioxa-8-nonenoyl fluoride by its fluorine water magnetic resonance spectrum.

The cold trap contained a small amount of material. Chlorine was condensed into the cold trap so that a higher boiling, more easily handleable mixture of products was obtained. The mixture, which totaled 2.4 g after chlorination, was separated by gas chromatography and the components issuing from the chromatography were analyzed by mass spectrometry. The components included tetrafluoroethylene, perfluoro-5-oxo-3-oxahexene and its chlorinated derivative 1,2-dichloro-1,1,2,4,4,6,6,6-octafluoro-5-oxo-3-oxahexane, perfluoro-5-methyl-4,7-dioxa-8-nonenoyl fluoride and 8H-perfluoro-5-methyl-3,6-dioxaoctene.

BEST MODE FOR CARRYING OUT THE INVENTION

The best modes presently contemplated for the invention are demonstrated in Examples 2 and 3 for the perfluoroketovinyl ether of formula 1, and its preparation, and in Example 7 for the copolymer prepared from the ether 1 and a vinyl monomer.

INDUSTRIAL APPLICABILITY

The perfluoroketovinyl ether 1 is used as a copolymerizable monomer from which fluorinated copolymers useful as molding resins can be prepared. The copolymers, after conversion by hydrolysis or other treatment, are also water-wettable, dyeable, possess ion-exchange properties and are useful in curable fluoroelastomer compositions.

Although the preferred embodiments of the invention have been illustrated and described above, it is to be understood that there is no intent to limit the invention to the precise constructions herein disclosed and it is to be further understood that the right is reserved to all changes and modifications coming within the scope of the invention as defined in the appended claims.

I claim:
1. Perfluoroketovinyl ether of the formula

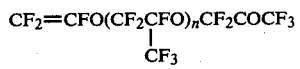

wherein n is an integer 1 to 4.
2. Perfluoroketovinyl ether of claim 1 wherein n is 1.
3. Process comprising heating the compound of the formula

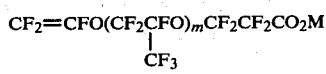

wherein M is an alkali or alkaline earth metal and m is an integer 2 to 5, at 130° C. to 300° C., in an aprotic solvent to produce the compound of claim 1.
4. Process of claim 3 wherein the temperature is 170° C. to 230° C. and the solvent is a glyme.
5. Process of claim 4 wherein the glyme is tetramethyleneglycol dimethyl ether.

* * * * *